United States Patent
Pang et al.

(10) Patent No.: US 7,384,926 B2
(45) Date of Patent: Jun. 10, 2008

(54) USE OF NON-FEMINIZING ESTROGENS AS RETINOPROTECTIVE AGENTS FOR THE TREATMENT OF GLAUCOMA

(75) Inventors: Iok-Hou Pang, Grand Prairie, TX (US); Abbot F. Clark, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/754,710

(22) Filed: May 29, 2007

(65) Prior Publication Data
US 2007/0225263 A1     Sep. 27, 2007

Related U.S. Application Data

(63) Continuation of application No. 10/487,122, filed as application No. PCT/US02/27969 on Sep. 3, 2002, now abandoned.

(60) Provisional application No. 60/317,225, filed on Sep. 5, 2001.

(51) Int. Cl.
*A61K 31/56* (2006.01)
(52) U.S. Cl. .................... 514/171; 514/182
(58) Field of Classification Search .................... None
See application file for complete search history.

(56) References Cited

U.S. PATENT DOCUMENTS

| 5,114,971 | A | 5/1992 | Stjernschantz et al. |
| 5,521,168 | A | 5/1996 | Clark |
| 5,843,934 | A | 12/1998 | Simpkins |
| 5,877,169 | A | 3/1999 | Simpkins |
| 6,197,833 | B1 | 3/2001 | Simpkins et al. |
| 2004/0214806 | A1 | 10/2004 | Pang et al. |

FOREIGN PATENT DOCUMENTS

| EP | 1236469 A2 | 9/2002 |
| EP | 1236469 A3 | 9/2002 |
| WO | 0242319 A2 | 5/2002 |
| WO | 0242319 A3 | 5/2002 |
| WO | 03020284 A1 | 3/2003 |

OTHER PUBLICATIONS

Bengtsson B, "Incidence of manifest glaucoma," Br J Ophthalmol, 73:483-487 (1989).
Caramazza et al., "Le modificazioni indotte da una associazione estrogeno-porgestinica sulla dinamica dell'umor acqueo nel glaucoma semplice", Ann Ottal 94, pp. 299-321 (1968).
Clark and Pang, "Advances in glaucoma therapeutics," Exp Opin Emerging Drugs, vol. 7, pp. 141-163 (2002).
Cyr et al., "Drugs with estrogen-like potency and brain activity: Potential therapeutic application for the CNS", Curr. Pharm. Design. vol. 6, pp. 1287-1312 (2000).
Emilien et al., "Prospects for pharmacological intervention in Alzheimer disease," Arch.Neurol, vol. 57, pp. 454-459 (2000).
European 02761551.7 Search Report dated Dec. 27, 2004.
Estrogen Receptor Structures & Functions, Biochemistry Course of the Carnegie Mellon University, Pittsburg, no date available.
Granholm, "Oestrogen and nerve growth factor—Neuroprotection and repair in Alzheimer's disease," Expert Opin. Invest. Drugs, vol. 9, pp. 685-694 (2000).
Green and Simpson, Annals of the New York Academy of Science 2000, 924, 93-98.
Green et al., "Neuroprotective effectives of phenolic A ring oestrogens," In Neuronal and Cognitive Effects of Oestrogens, Wiley & Sons, New York, pp. 202-220 (2000).
Green et al., Endocrinology 2001, 142, 400-406.
Greve and Chisholm, "Comparison of the oculokinetic perimetry glaucoma screener with two types of visual field analyser," Can J Ophthalmol, vol. 28, pp. 201-206 (1993).
Harrison's Principles of Internal Medicine, 13th edition, vol. 1, published 1994, pp. 104-105.
Henderson VS, "Estrogen replacement therapy for the prevention and treatment of Alzheimer's disease," CNS Drugs, vol. 8, pp. 343-351 (1997).
Honjo et al., Endocrine Journal 2003, 50 (4), 361-367.
Kobayashi et al., "Estrogen receptor expression in bovine and rat retinas," Invest. Ophthalmol. Vis. Sci., vol. 39, pp. 2105-2110 (1998).
Kumar et al., Free Radical Biology and Medicine 2005, 38, 1152-1163.
Langham ME, "The physiology and pathology of the intraocular pressure," In Glaucoma: Contemporory International Concepts, Ed. Bellows, JG, Masson Publishing, New York, pp. 24-48 (1979).
Leske et al, "The Barbados Eye Study. Prevalence of open angle glaucoma," Arch Ophthalmol, vol. 112, pp. 821-829 (1994).
Leske et al, "Distribution of intraocular pressure. The Barbados Eye Study," Arch Ophthalmol, vol. 115, pp. 1051-1057 (1997).

(Continued)

Primary Examiner—Raymond J. Henley, III
(74) Attorney, Agent, or Firm—Teresa J. Schultz

(57) ABSTRACT

The invention provides pharmaceutical compositions containing non-feminizing estrogen and methods of using these compositions to prevent or ameliorate retinal and optic nerve damage associated with glaucoma.

3 Claims, No Drawings

OTHER PUBLICATIONS

Leske et al, "Incidence of open-angle glaucoma: the Barbados Eye Studies. The Barbados Eye Studies Group," Arch Ophthalmol, vol. 119, pp. 89-95 (2001).

McMillan and Dorsa, "Estrogen actions in the central nervous system," Curr. Opin. Endocrinol. Diabetes, vol. 6, pp. 33-37 (1999).

Meyers et al., "Influence of norethynodrel with mestranol on intraocular pressure in glaucoma", ACTA Ophthalmol 75:157-161 (1966).

Monk and Brodaty, "Use of estrogens for the prevention and treatment of Alzheimer's disease," Dementia Geriatr Cogn Disord, vol. 11, pp. 1-10 (2000).

Ogueta et al., "Estrogen receptor in the human eye: influence of gender and age on gene expression," Invest. Ophthalmol. Vis. Sci., vol. 40, pp. 1906-1911 (1999).

PCT/US02/27969 PCT International Search Report dated Jan. 30, 2003.

Qureshi IA, "Ocular hypertensive effect of menopause with and without systemic hypertension", ACTA Obstet Gynecol Scand 75:266-269 (1996).

Rao BR, "Isolation and characterization of an estrogen binding protein which may integrate the plethora of estrogenic actions in non-reproductive organs," J. Steroid Biochem. Mol. Biol., vol. 65, pp. 3-41 (1998).

Rohen, "Why is intraocular pressure elevated in chronic simple glaucoma? Anatomical considerations," Ophthalmology, vol. 90, pp. 758-765 (1983).

Sator MO et al., "Hormone replacement therapy and intraocular pressure", Maturitas 28:55-58 (1997) XP002309890 abstract.

Sator et al., "Reduction of intraocular pressure in a glaucoma patient undergoing hormone replacement therapy", Maturitas vol. 29, pp. 93-95 (1998).

Segawa K, (1979) "Electron microscopic changes in the trabecular tissue in primary open angle glaucoma," In Glaucoma: Contemporory International Concepts, Ed. Bellows JG, Masson Publishing, New York, pp. 17-23 (1979).

Simpkins et al., "Neuroprotective effects of estrogens", In Biology of Menopause, Ed. Bellino FL. Springer-Verlag, New York, pp. 103-111 (2000).

Simpkins et al., Annals of the New York Academy of Science 2005, 1052, 233-242.

Stedman's Medical Dictionary, 25th edition, published 1990, pp. 1351-1351.

Strong, N. P., "How optometrists screen for glaucoma: A survey", Ophthal. Physiol. Opt., 12:3-7 (1992).

Tanna and Jampel, "Normal-tension glaucoma," Ophthalmol Clinics North Am, vol. 13, pp. 455-464 (2000).

The Merck Index, 11th Edition, published 1989, pp. 583-585.

Treister and Mannor, "Intraocular pressure and outflow facility—effect of estrogen and combined estrogen-progetin treatment in normal human eyes", Arch Ophthalmol 83, pp. 311-318 (1970).

US Food and Drug Administration, "Predictive Models" (http://edkb.fda.gov/models.html), no date available.

Wang et al., "Estrogen provides neuroprotection in transient forebrain ischemia through perfusion-independent mechanisms in rats," Stroke, vol. 30, pp. 630-637 (1999).

Wickham et al., "Identification of androgen, estrogen and progesterone receptor mRNAs in the eye," ACTA. Ophthalmol. Scand., vol. 78, pp. 146-153 (2000).

Woolly CS, "Electrophysiological and cellular effects of estrogen on neuronal function," Crit. Rev. Neurobiol., vol. 13, pp. 1-20 (1999).

Worda and Sator, "Hormone replacement therapy and its effect on the eye", J Menopause 3:24-27 (1999).

Yamamoto and Kitazawa, "Vascular pathogenesis of normal-tension glaucoma: a possible pathogenetic factor, other than intraocular pressure, of glaucomatous optic neuropathy," Prog Retin Eye Res, vol. 17, pp. 127-143 (1998).

USE OF NON-FEMINIZING ESTROGENS AS RETINOPROTECTIVE AGENTS FOR THE TREATMENT OF GLAUCOMA

This continuation application claims priority from a U.S. patent application Ser. No. 10/487,122 filed Feb. 19, 2004 now abandoned, which is a 371 of PCT/US02/27969 filed Sep. 3, 2002, which claims benefit of U.S. Provisional Patent Application Ser. No. 60/317,225, filed on Sep. 5, 2001.

BACKGROUND OF THE INVENTION

1. Field of the Invention

The present invention relates to the field of glaucoma. More specifically, the invention provides a method to protect glaucomatous retinopathy using compositions comprising at least one non-feminizing estrogen.

2. Description of the Related Art

"Glaucomas" are a group of debilitating eye diseases that are the leading cause of preventable blindness in the United States and other developed nations. Primary Open Angle Glaucoma (POAG) is the most common form of glaucoma. The disease is characterized by the degeneration of the trabecular meshwork (TM), leading to obstruction of the normal ability of aqueous humor to leave the eye without closure of the space (e.g., the "angle") between the iris and cornea (Langham (1979); Segawa (1979); Rohen (1983)). A characteristic of such obstruction in this disease is an increased intraocular pressure (IOP), resulting in progressive visual loss and blindness if not treated appropriately and in a timely fashion. The disease is estimated to affect between 0.4% and 3.3% of all adults over 40 years old (Leske et al. (1994, 1997, 2001); Bengtsson (1989); Strong (1992)). Moreover, the prevalence of the disease rises with age to over 6% of those 75 years or older (Strong (1992)).

Another form of POAG, normal-tension glaucoma, is characterized by a severe optic neuropathy in the absence of abnormally high IOP. Patients with normal-tension glaucoma have pressures within the normal range, albeit often in the high normal range (Tanna & Jampel (2000)).

Because increased IOP is a readily measurable characteristic of glaucoma, the diagnosis of the disease is largely based on an increase in IOP which is generally estimated by tonometry (Strong (1992); Greve & Chisholm (1993)). Unfortunately, as is evident from normal-tension glaucoma, glaucomatous retinopathy and optic nerve damage can occur in the absence of abnormally high IOP (Yamamoto & Kitazawa (1998); Tanna & Jampel (2000)). Conversely, ocular hypertension does not always lead directly to retina or optic nerve damage. Approximately 5 million Americans have elevated IOP without optic nerve damage or visual field loss. Because the relationship between pressure and optic nerve and retina damage is not necessarily direct, high IOP is now considered to be only a risk factor rather than an essential disease characteristic. For this reason, additional methods, such as direct examination of the optic disk and determination of the extent of a patient's visual field loss are often conducted to improve the accuracy of diagnosis (Greve & Chisholm (1993)). Also for the same reason, the ultimate goal of glaucoma treatment is to preserve vision by protecting against the pathological changes in the retina and optic nerve.

Current glaucoma therapy is directed to lowering IOP. A variety of therapeutic agents have been proposed as having the ability to reduce elevated IOP. These therapies lower IOP, but they do not directly address the pathogenic mechanisms occurring at the retina and optic nerve, and the disease continues to progress. Moreover, many of these agents are often associated with untoward effects. There is currently no generally accepted therapeutic method to manage glaucomatous retinopathy and optic neuropathy. Agents offering retinoprotection properties would be desirable.

SUMMARY OF THE INVENTION

The present invention overcomes these and other drawbacks of the prior art by providing compositions comprising at least one non-feminizing estrogen or its analogs and methods for their use in the treatment of glaucomatous retinopathy. In particular, the invention provides methods for retinoprotection by administering to a patient in need thereof a therapeutically effective amount of a composition including at least one non-feminizing estrogen compound or an analog thereof. As used herein, the phrase "non-feminizing estrogen compound" refers to compounds having very little or no feminizing, or sex-related, activity.

It is contemplated that virtually any non-feminizing estrogen compound will be useful in the methods of the invention. Typically, the non-feminizing estrogen compound for use in the methods of the invention will be polycyclic compounds having a terminal phenolic group, in a structure containing at least a second ring, having a molecular mass of less than 1000 Daltons. Examples of such compounds include, but are not limited to, estratriene-3-ol, 3,17α-estradiol, estrone, estriol, and their analogs. Most preferably, the non-feminizing estrogen compound is estratriene-3-ol.

DETAILED DESCRIPTION PREFERRED EMBODIMENTS

Incidence of ocular hypertension and primary open angle glaucoma is known to increase during menopause (Qureshi (1996); Worda & Sator (2000)), which may be related to the sudden decrease of circulating concentration of estrogen in post-menopausal women. Administration of estrogen together with progestin was shown to lower IOP (Meyer et al. (1966); Caramazza et al. (1968); Treister & Mannor (1970); Sator et al. (1998)). Treister and Mannor also observed the IOP-lowering effect with estrogen administration alone (1970). The estrogen-induced reduction in IOP correlates with an increase in outflow facility of aqueous humor. However, independent of the IOP-lowering effect, estrogens have been demonstrated to be protective against various insults in the brain (Cyr et al. (2000); Emilien et al. (2000); Granholm (2000); Green et al. (2000); Henderson (1997); McMillan & Dorsa (1999); Monk & Brodaty (2000); Simpkins et al. (2000); Woolly (1999)). Estrogen receptor (Kobayashi et al. (1998); Ogueta et al. (1999); Wickham et al. (2000)) and an estrogen-binding protein (Rao (1998)) have been found in the retina. It is likely that estrogen receptor is involved in vision-affecting conditions in the retina. The present inventors contemplate for the first time that estrogens are useful in the prevention, treatment or reduction of retina and optic nerve damages associated with glaucoma independent of their effects on IOP.

Classical estrogens or their metabolites are not practical as therapeutic agents for the treatment of retinal diseases because their feminizing effects are not acceptable to many patients. Non-feminizing estrogen compounds are estrogen-related compounds having substantially no sex-related effect on the subject. Simpkins et al. (U.S. Pat. No. 6,197,833; U.S. Pat. No. 5,877,169; U.S. Pat. No. 5,843,934 all incorporated herein by reference) discuss the use of such compounds for treatment of patients with a number of degenerative conditions or conditions resulting from ischemic damage in the brain. Simpkins et al. do not discuss the use of the compounds for the treatment of eye-related diseases.

Estrogen occurs in at least two isomeric forms, including α estrogen and β estrogen. β estrogens are pleotrophic molecules with many biological activities. Clinical uses include treatment of osteoporosis, symptoms of menopause and fertility control. In comparison to β estrogen, α estrogen is typically believed to be at least 100-1000 times less potent in estrogenic activity. Numerous examples have been reported in the literature that show that the biological effects of β estrogen are not shared by the α isomer. In fact, in the art, α estrogen is typically used as a negative control for β estradiol.

Simpkins et al. (U.S. Pat. No. 5,843,934, herein incorporated by reference) showed the α estrogen has a comparable activity to that of β estrogen for neuroprotection. This activity provides α estrogen with a number of advantages over β estrogen in the treatment of degenerative diseases, trauma and aging related to the central nervous system. These advantages arise in situations which require treatment of males where the development of female traits is to be avoided and the treatment of females where the subject has increased susceptibility to endometrial, breast and cervical cancer. The present inventors show for the first time that non-feminizing estrogens are useful in the treatment of glaucomatous retinopathy.

U.S. Pat. No. 5,521,168 discusses the use of estrogen metabolites for lowering of intraocular pressure. The compounds disclosed in this patent are estrogen metabolites, some of which may not have sex-related pharmacological actions. However, U.S. Pat. No. 5,521,168 does not discuss the use of these estrogen metabolites or any non-feminizing estrogens in the treatment of glaucoma-related retina and optic nerve damages.

It is contemplated that virtually any non-feminizing estrogen compound will be useful in the methods of the invention. Typically, the non-feminizing estrogen compound for use in the methods of the invention will be a polycyclic compound having a terminal phenolic group, in a structure containing at least a second ring, having a molecular mass of less than 1000 Daltons. Examples of such compounds include, but are not limited to, estratriene-3-ol, 3,17α-estradiol, estrone, estriol, and their analogs. Most preferably, the non-feminizing estrogen compound is estratriene-3-ol.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The compositions of the present invention comprise one or more non-feminizing estrogens and a pharmaceutically acceptable vehicle. As used herein, the term "pharmaceutically acceptable vehicle" refers to any formulation which is acceptable, i.e., safe and provides the appropriate delivery for the desired route of administration, of an effective amount of one or more non-feminizing estrogens. The compositions of the present invention may be administered in a variety of different ways including systemically (e.g., oral administration, intramuscular injection, subcutaneous injection, intravenous injection, transdermal administration and transmucosal administration), topically and by intraocular injection, intraocular perfusion, periocular injection or retrobulbar (sub-tenon) injection.

The exact dosage of the non-feminizing estrogen(s) will vary, but will be determined by skilled clinicians in the art. Various factors affecting the dosage amount include the actual disease to be treated, the severity of condition, the health of the patient, the potency and specific efficacy of the non-feminizing estrogen, and so on. The amount dosed, however, will be in an effective to prevent, treat or ameliorate an ocular disease or disorder, e.g., those described herein; such an amount is referred herein as an "effective amount." In general, the daily dosage of non-feminizing estrogens will range between about 0.001 and 100 milligrams per kilogram body weight per day (mg/kg/day), and preferably between about 0.01 and 5.0 mg/kg/day.

The non-feminizing estrogens of the present invention may be contained in various types of ophthalmic compositions, in accordance with formulation techniques known to those skilled in the art. For example, the compounds may be included in solutions, suspensions and other dosage forms adapted for topical, intravitreal or intracameral use.

Aqueous compositions are generally preferred, based on ease of formulation and physiological compatibility. However, the non-feminizing estrogens of the present invention may also be readily incorporated into other types of compositions, such as suspensions and viscous or semi-viscous gels or other types of solid or semi-solid compositions for topical or retrobulbar injection. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Topical ophthalmic products are typically packaged in multi-dose form. Preservatives are thus required to prevent microbial contamination during use. Suitable preservatives include: benzalkonium chloride, chlorobutanol, methyl paraben, propyl paraben, phenylethyl alcohol, edetate disodium, sorbic acid, polyquaternium-1, or other agents known to those skilled in the art. Some of these preservatives, however, may be unsuitable for particular applications, (e.g., benzalkonium chloride may be unsuitable for intraocular injection). Such preservatives are typically employed at a level of from 0.001 to 1.0% weight/volume ("% w/v").

For topical administration of non-feminizing estrogens, the typical dosage generally will range between about 1-2 two drops administered to the eye 1-4 times per day of a composition comprising 0.001 and 5% weight/volume ("w/v"), and preferably between 0.1 and 1% (w/v) of one or more non-feminizing estrogens. Solutions, suspensions, ointments, gels, jellies and other dosage forms adapted for topical administration are preferred. Additionally, non-feminizing estrogens may be delivered slowly, over time, to the afflicted tissue of the eye through the use of contact lenses. This regimen is generally performed by first soaking the lenses in a non-feminizing estrogen solution, and then applying the contact lenses to the eye for normal wear.

The compositions of the present invention are further illustrated in the following formulation examples, non-feminizing estrogens of the present invention are represented generically in the examples as "non-feminizing estrogen."

Example 1

A topical ophthalmic composition useful for treating retinal vascular diseases:

| Ingredient | Concentration (% w/v) |
| --- | --- |
| Non-feminizing estrogen | 0.1 |
| Dibasic Sodium Phosphate | 0.2 |
| HPMC | 0.5 |
| Polysorbate 80 | 0.05 |
| Benzalkonium Chloride | 0.01 |
| Sodium Chloride | 0.75 |
| Edetate Disodium | 0.01 |
| NaOH/HCl | q.s., pH 7.4 |
| Purified Water | q.s. 100% |

Example 2

A sterile intraocular injection solution useful for treating retinal vascular diseases:

| Ingredient | Concentration (% w/v) |
| --- | --- |
| Non-feminizing estrogen | 0.05-5.0 |
| Cremophor EL ® | 10 |
| Tromethamine | 0.12 |
| Mannitol | 4.6 |
| Disodium EDTA | 0.1 |
| Hydrochloric acid or sodium hydroxide | q.s., pH to 7.4 |
| Water for injection | q.s. 100% |

Example 3

A tablet formulation suitable for oral administration, and useful for treating retinal vascular diseases:

| Ingredient | Amount per Tablet (mg) |
| --- | --- |
| Non-feminizing estrogen | 200 |
| Cornstarch | 50 |
| Lactose | 145 |
| Magnesium stearate | 5 |

Example 4

An systemic injectable solution useful for treating retinal vascular diseases:

| Ingredient | Amount |
| --- | --- |
| Non-feminizing estrogen | 200 mg |
| 0.4M KH2PO4 solution | 2 ml |
| 1N KOH solution | q.s. to pH 7.0 |
| Water for injection | q.s. to 20 ml |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

United States Patents
U.S. Pat. No. 5,521,168
U.S. Pat. No. 5,843,934
U.S. Pat. No. 5,877,169
U.S. Pat. No. 6,197,833

Books

Green and Simpkins "Neuroprotective effectives of phenolic A ring oestrogens," In NEURONAL AND COGNITIVE EFFECTS OF OESTROGENS, Wiley & Sons, New York, pp 202-220 (2000)

Langham M E, "The physiology and pathology of the intraocular pressure," In GLAUCOMA: CONTEMPORORY INTERNATIONAL CONCEPTS, Ed. Bellows, J G, Masson Publishing, New York, pp 24-48 (1979).

Segawa K, (1979) "Electron microscopic changes in the trabecular tissue in primary open angle glaucoma," In GLAUCOMA: CONTEMPORORY INTERNATIONAL CONCEPTS, Ed. Bellows J G, Masson Publishing, New York, pp 17-23 (1979)

Simpkins J W, Green P S, Gridley K E, Shi J, Monck E K, "Neuroprotective effects of estrogens," In BIOLOGY OF MENOPAUSE, Ed. Bellino F L, Springer-Verlag, N.Y., pp 103-111 (2000).

Other Publications

Bengtsson, "Incidence of manifest glaucoma," BR J OPHTHALMOL, vol 73, pp 483-487 (1989)

Caramazza et al, "Le modificazioni indotte da una associazione estrogeno-progestinica sulla dinamica dell'umor acqueo nel glaucoma semplice," ANN OTTAL, vol 94, pp 299-311 (1968)

Cyr et al, "Drugs with estrogen-like potency and brain activity: Potential therapeutic application for the CNS," CURR PHARM DESIGN, vol 6, pp 1287-1312 (2000)

Emilien et al, "Prospects for pharmacological intervention in Alzheimer disease," ARCH NEUROL, vol 57, pp 454-459 (2000)

Granholm, "Oestrogen and nerve growth factor—Neuroptrotection and repair in Alzheimer's disease," EXPERT OPIN INVEST DRUGS, vol 9, pp 685-694 (2000)

Greve and Chisholm, "Comparison of the oculokinetic perimetry glaucoma screener with two types of visual field analyser," CAN J OPHTHALMOL, vol 28, pp 201-6 (1993)

Henderson, "Estrogen replacement therapy for the prevention and treatment of Alzheimer's disease," CNS DRUGS, vol 8, pp 343-351 (1997).

Kobayashi et al, "Estrogen receptor expression in bovine and rat retinas," INVEST OPHTHALMOL VIS SCI, vol 39, pp 2105-2110 (1998).

Leske et al, "*The Barbados Eye Study. Prevalence of open angle glaucoma*," ARCH OPHTHALMOL, vol 112, pp 821-829 (1994)

Leske et al, "*Distribution of intraocular pressure. The Barbados Eye Study*," ARCH OPHTHALMOL, vol 115, pp 1051-1057 (1997)

Leske et al, "*Incidence of open-angle glaucoma: the Barbados Eye Studies. The Barbados Eye Studies Group*," ARCH OPHTHALMOL, Vol 119, pp 89-95 (2001)

McMillan and Dorsa, "*Estrogen actions in the central nervous system*," CURR OPIN ENDOCRINOL DIABETES, vol 6, pp 33-37 (1999)

Meyer et al, "*Influence of norethynodrel with mestranol on intraocular pressure in glaucoma*," ARCH OPHTHALMOL, vol 75, pp 157-161 (1996)

Monk and Brodaty, "*Use of estrogens for the prevention and treatment of Alzheimer's disease*," DEMENTIA GERIATR COGN DISORD, vol 11, pp 1-10 (2000)

Ogueta S B, Schwartz S D, Yamashita C K, Farber D B, "*Estrogen receptor in the human eye: influence of gender and age on gene expression*," INVEST OPHTHALMOL VIS SCI, vol 40, pp 1906-1911 (1999)

Qureshi, "*Ocular hypertensive effect of menopause with and without systemic hypertension*," ACTA OBSTET GYNECOL SCAND, vol 75, pp 266-269 (1996).

Rao, "*Isolation and characterization of an estrogen binding protein which may integrate the plethora of estrogenic actions in non-reproductive organs*," J STEROID BIOCHEM MOL BIOL, vol 65, pp 3-41 (1998)

Rohen, "*Why is intraocular pressure elevated in chronic simple glaucoma? Anatomical considerations*," OPHTHALMOLOGY, vol 90, pp 758-765 (1983)

Sator et al, "*Reuction of intraocular pressure in a glaucoma patient undergoing hormone replacement therapy*," MATURITAS, vol 29, pp 93-95 (1998)

Strong, "*How optometrists screen for glaucoma: a survey*," OPHTHALMIC PHYSIOL OPT, vol 12, pp 3-7 (1992)

Tanna and Jampel, "*Normal-tension glaucoma*," OPHTHALMOL CLINICS NORTH AM, vol 13, pp 455-464 (2000)

Treister and Mannor, "*Intraocular pressure and outflow facility—effect of estrogen and combined estrogen-progestin treatment in normal human eyes*," ARCH OPHTHALMOL, Vol 83, pp 311-318 (1970)

Wang et al., "*Estrogen provides neuroprotection in transient forebrain ischemia through perfusion-independent mechanisms in rats*," STROKE, vol 30, pp 630-637 (1999)

Wickham et al., "*Identification of androgen, estrogen and progesterone receptor mRNAs in the eye*," ACTA OPHTHALMOL SCAND, Vol 78, pp 146-153 (2000)

Woolley, "*Electrophysiological and cellular effects of estrogen on neuronal function*," CRIT REV NEUROBIOL, 13:1-20 (1999)

Worda & Sator, "*Hormone replacement therapy and its effect on the eye*," J MENOPAUSE, vol 3, pp 24-27 (1999)

Yamamoto and Kitazawa, "*Vascular pathogenesis of normal-tension glaucoma: a possible pathogenetic factor, other than intraocular pressure, of glaucomatous optic neuropathy*," PROG RETIN EYE RES, vol 17, pp 127-43 (1998)

We claim:

1. A method for treating glaucoma-related retina or optic nerve damage in a patient, said method comprising administering to a patient in need thereof a composition comprising a therapeutically effective amount of at least one non-feminizing estrogen compound, wherein said non-feminizing estrogen compound is selected from the group consisting of estratriene-3-ol, 3,17α-estradiol, estrone, and estriol, and wherein said composition is administered via a method selected from the group consisting of intravitreal injection, intraocular perfusion, periocular injection and sub-Tenon injection.

2. The method of claim 1, wherein said glaucoma is primary open angled glaucoma.

3. The method of claim 1, wherein said composition is administered via intravitreal injection.

* * * * *